United States Patent [19]
McGrath et al.

[11] Patent Number: 6,149,918
[45] Date of Patent: *Nov. 21, 2000

[54] HUMAN HERPESVIRUS TYPE 8 ISOLATED FROM HUMAN LYMPHOMA CELL LINE

[75] Inventors: Michael S. McGrath; Brian Herndier, both of Burlingame; Valerie L. Ng, Piedmont; Donald E. Ganem, San Francisco, all of Calif.

[73] Assignee: The Regents of the University of California, Oakland, Calif.

[ * ] Notice: Under 35 U.S.C. 154(b), the term of this patent shall be extended for 160 days.

[21] Appl. No.: 08/529,881

[22] Filed: Sep. 18, 1995

[51] Int. Cl.$^7$ ........................ A61K 39/245; A61K 39/12; C12N 7/00
[52] U.S. Cl. .................... 424/229.1; 424/204.1; 435/5; 435/235.1; 435/238
[58] Field of Search ........................ 435/5, 235.1, 240.1, 435/240.2, 284, 238; 424/204.1, 229.1

[56] References Cited

U.S. PATENT DOCUMENTS 5,830,759  11/1998  Chang et al. ........................ 435/372.2

OTHER PUBLICATIONS

Boshoff et al., Lancet, 345 : 1043–1045, Apr. 22, 1995.
Biesinger et al., PNAS USA, 89: 3116–3119, Apr. 1992.
Flemington et al., J. Virol., 64(9): 4549–4552, Sep. 1990.
Cesarman, Ethel. et al., "Kaposi's Sarcoma—Associated Herpesvirus–like DNA Sequences in AIDS–Related Body–Cavity–Based Lymphomas", (May 4, 1995), *N. Engl. J. Med.,* vol. 332, No. 18 pp. 1186–1191.
Chang, Yuan, et al., "Identification of Herpesvirus–Like DNA Sequences in AIDS–Associated Koposi's Sarcoma", (Dec. 16, 1994), *Science,* vol. 266, pp. 1865–1869.
Chadburn, Amy, et al., "CD30 (Ki–1) Positive Anaplastic Large Cell Lymphomas in Individuals Infected with the Human Immunodeficiency Virus", (Nov. 15, 1993) *Cancer,* vol. 72, No. 10, pp. 3078–3090.
Dambaugh, Timothy, et al., "Epstein–Barr virus (B95–8) DNA VII: Molecular cloning and detailed mapping", (May 1980) *Proc. Natl. Acad. Sci. (USA),* vol. 77, No. 5, pp. 2999–3003.
Green, I., et al., "Primary Lymphomatous Effusions in AIDS: A Morphological, Immunophenotypic, and Molecular Study", (1995) *Modern Pathol.,* vol. 8, No. 1, pp. 39–45.
Herndier, Brian G., et al., "Acquired Immunodeficiency Syndrome–Associated T–Cell Lymphoma: Evidence for Human Immunodeficiency Virus Type 1–Associated T–Cell Transformation" (Apr. 1, 1992) *Blood,* vol. 79, No. 7, pp. 1768–1774.
Knowles, Daniel M., et al., "Molecular Genetic Analysis of Three AIDS–Associated Neoplasms of Uncertain Lineage Demonstrates Their B–Cell Derivation and the Possible Pathogenetic Role of the Epstein–Barr Virus", (Feb. 15, 1989) *Blood,* vol. 73, No. 3, pp. 792–799.
Moore, Patrick S., et al., "Detection of Herpesvirus–like DNA Sequences in Kaposi's Sarcoma in Patients with and Those Without HIV Infection", (May 4, 1995), *N. Engl. J. Med.,* vol. 332, No. 18, pp. 1181–1185.
Ng, Valerie, L., "IgMs Produced by Two Acquired Immune Deficiency Syndrome Lymphoma Cell LInes: Ig Binding Specificity and $V_H$–Gene Putative Somatic Mutation Analysis", (Feb. 15, 1994), *Blood,* vol. 83, No. 4, pp. 1067–1078.
Ng. Valerie, L., Erratum to: ["IgMs Produced by Two Acquired Immune Deficiency Syndrome Lymphoma Cell LInes: Ig Binding Specificity and $V_H$–Gene Putative Somatic Mutation Analysis", (Feb. 15, 1994, *Blood,* vol. 83, No. 4, pp. 1067–1078], (Aug. 1, 1994), *Blood,* vol. 84, No. 3, p. 995.
Walts, Ann E., et al., "Diagnosis of Malignant Lymphoma in Effusions from Patients with AIDS by Gene Rearrangement", (Aug. 1990) *A. J. Clin. Pathol.* vol. 94, No. 2: pp. 170–175.

*Primary Examiner*—Ali R. Salimi
*Attorney, Agent, or Firm*—Bozicevic, Field & Francis, LLP

[57] ABSTRACT

A human lymphoma cell line containing a human herpesvirus type 8 (HHV-8) capable of in vitro growth and which produces HHV-8 virus particles upon induction of lytic viral growth is provided. Virus produced by the cell line of the invention is useful for the production of antibodies to an HHV-8 virus particle, viral protein, or viral peptide. Methods of screening a biological sample for the presence of HHV-8 virus particles, viral protein, or viral peptide from a human suspected of being infected with HHV-8 are provided as are methods of screening a biological sample of the human for antibodies to HHV-8.

8 Claims, 1 Drawing Sheet

```
KSHV   AGCCGAAAGG ATTCCACCAT TGTGCTCGAA TCCAACGGAT TGACCCCGT GTTCCCCATG GTCGTGCCGC AGCAACTGGG
                10         20         30         40        50         60         70         80

KSHV   GCACGCTATT CTGCAGCAGC TGTTGGTGTA CCACATCTAC TCCAAAATAT CGGCCGGGGC CCCGGATGAT GTAAATATGG
                90        100        110        120        130        140        150        160

KSHV   CGGAACTTGA TCTATATACC ACCAATGTGT CATTTATGGG GCGCACATAT CGTCTGGACG TAGACAACAC GGA
               170        180        190        200        210        220        230

(Seq. I.D. No.1)
```

FIG 1

HUMAN HERPESVIRUS TYPE 8 ISOLATED FROM HUMAN LYMPHOMA CELL LINE

STATEMENT AS TO FEDERALLY SPONSORED RESEARCH

This invention was made with Government support under Grant No. CA67381-01, awarded by the National Institutes of Health, and a grant from the Howard Hughes Institute. The Government has certain rights in this invention.

FIELD OF THE INVENTION

The present invention relates to a human lymphoma cell line containing a human herpesvirus, and in particular, to a novel type of human herpesvirus associated with human body cavity-based lymphoma.

BACKGROUND OF THE INVENTION

Individuals infected with the human immunodeficiency virus, type 1 (HIV-1) are at a 60–100 fold increased risk of developing lymphoma as compared to the general population. This risk is likely to increase as a result of improvements in supportive care for opportunistic infections and use of antiretroviral therapy (Gill, P. S. et al. (1987) J. Clin Oncol. 5:1322; Gail, M. H., et al. (1991) J. Natl. Cancer Inst. 83695).

The majority of HIV-associated lymphomas are of B-cell origin and constitute a heterogeneous group of lymphomas (Shiramizu, B. T. et al. (1992) J. Clin. Oncol. 10:383; Levine A. M. et al. (1991) Cancer 68:2466). Primary lymphomas arising in the central nervous system (CNS) typically occur in HIV-1 infected individuals with advanced disease who have had multiple opportunistic infections and have few peripheral CD4+ lymphocytes; the majority of these lymphomas are monoclonal and infected with Epstein-Barr virus (EBV). In contrast, lymphomas arising outside of the CNS often occur in HIV-1 infected individuals who are relatively more immunocompetent and who often have had no prior opportunistic infections. Of these peripheral lymphomas, 30% are polyclonal and lack evidence of EBV infection.

A rare and unique subset of HIV-1 associated lymphomas arising only in body cavities (i.e., peritoneal, pleural, pericardial) has been described (Walts, A. E. et al. (1990) J. Clin. Pathol. 94:170; Knowles, D. M. et al. (1989) Blood 73:792; Chadburn, A. et al. (1993) Cancer 72:3078; Green, I. et al. (1995) Modern Pathol. 8:39). These body cavity based (BCB) lymphomas display a marked propensity for invasion of the pleural or peritoneal cavities where they grow as ascites tumors.

Recently, viral sequences from human herpesvirus, type 8 (HHV-8) were found in six BCB lymphomas (Cesarman, E. et al. (1995) N. Engl. J. Med. 332:1186). HHV-8 is a virus originally discovered in association with Kaposi's sarcoma (KS) in HIV-infected individuals (Moore, P. S. and Chang, Y. (1995) New Engl. J. Med. 332:1181–1185). However, there has been no systematic description of the clinical features, management and outcomes of patients with HIV-associated BCB lymphomas.

In view of the association of a human herpesvirus type 8 with an AIDS-associated BCB lymphoma, there is a need for a cell line containing the human herpesvirus type 8 virus, and from which virus particles can be isolated. This convenient source of a novel virus would allow the generation of antibodies against the agent, screening of a patient or blood supplies for the virus or for antibodies to the virus, and lead to possible preclinical treatment of disease associated with the viral agent.

SUMMARY OF THE INVENTION

An isolated, intact virus associated with body cavity based lymphoma and Kaposi's sarcoma, a cell line containing the virus and assays prepared using the virus or a portion thereof are disclosed.

In one embodiment, the invention provides a novel human B cell lymphoma cell line isolated from a body cavity tumor of a patient with body cavity based lymphoma (BCB lymphoma) preferably the cell line designated BCBL-1 (ATCC CRL 11982). The cell line of the invention contains a BCB lymphoma-associated human herpesvirus type 8 (herein designated HHV-8). The cell line can be grown in culture and used for the production of HHV-8 which can be used to produce assays for detecting antibodies which bind to HHV-8. The cell line is characterized by its ability to produce large amounts of HHV-8. The isolated, intact HHV-8 contained within or isolated from a cell of the invention is characterized as a herpesviral particle of approximately 100 nm diameter, and having a viral genome visible by transmission electron microscopy as an electron-dense central icosahedral toroid core. DNA of the HHV-8 isolated from cells of the invention hybridizes to a 233 kb KSHV DNA sequence (Moore, P. S. and Chang, Y. (1995) New Engl. J. Med. 332:1181–1185, herein incorporated by reference specifically with respect to FIG. 2) SEQ ID NO:1.

In a related embodiment, the cell line of the invention is designated BCBL-1 (ATCC CRL 11982). The human from which the HHV-8-containing cell line is isolated also may be infected with a human immunodeficiency virus (such as HIV-1). The body cavities from which the cell line of the invention may be isolated includes the peritoneal cavity, the pleural cavity, or the pericardial cavity of the patient.

It is an advantage that the cell line of the present invention does not contain an Epstein Barr Virus (EBV). As a result, preparations isolated, intact HHV-8 particles isolated from the cell line of the present invention do not contain EBV particles or EBV proteins. The cell line is therefore useful as a source of HHV-8 for use in methods of screening a biological sample such as a cell or a body fluid of individuals who may be at risk for developing lymphoma. Blood supplies also may be screened prior to use in transfusion so that recipients will not be infected by HHV-8.

In a second embodiment, the invention provides a human herpesvirus type 8 isolated from a human B-lymphoma cell. The HHV-8 of the invention is characterized as a herpesviral particle of approximately 100 nm diameter, having a viral genome visible by electron microscopy as an electron-dense central icosahedral toroid, and the DNA of the virus hybridizing to DNA of SEQ ID NO:1. The HHV-8 of the invention is further characterized as being contained within or isolated from a cell from a body cavity based lymphoma of a human (for example, a patient also infected with a human immunodeficiency virus). The HHV-8 of the invention has the characteristics of a human herpesvirus from a BCBL-1 cell and a specific isolate of the virus is contained within ATCC deposit CRL 11982.

In yet another embodiment, the invention provides an antibody that specifically binds to a human herpesvirus type 8, which virus is associated with human body cavity based lymphoma. Preferably, the antibody is raised to a protein of a human herpesvirus isolated from a cell line designated BCBL-1. The antibody of the invention is described as an anti-HHV-8 antibody and is raised against an isolated virus particle or an immunogenic portion of the virus, such as an isolated immunogenic viral protein (or peptide).

Determination of immunogenicity of a protein and generation of an antibody to a virus or a protein are techniques well known in the art (see, for example Harlow and Lane, 1988, supra). By "immunogenic portion" is meant a portion of a virus, such as an HHV-8 virus, which portion is of sufficient size and/or conformation that when injected into an animal causes an immune response and antibodies are generated which bind to the immunogenic portion.

By "specifically binds", as used herein, is meant an agent, such as an antibody, which binds a human herpesvirus type 8 virus particle, viral protein, viral peptide, but which does not substantially bind other molecules in a sample, e.g., a biological sample, which naturally includes other proteins. Preferably such an antibody specifically and selectively binds to HHV-8.

In still another embodiment, the invention provides an isolated immunogenic polypeptide from a human herpesvirus type 8. Preferably, the polypeptide is encoded by a human herpesvirus contained in a body cavity based B lymphoma cell. More preferably, the virus is contained in a cell line designated BCBL-1. The immunogenic polypeptide is isolated from a cell lysate containing the virus, isolated from a preparation of isolated virus particles, or expressed from DNA cloned from the virus. The polypeptide is purified by standard protein purification techniques known to those of ordinary skill in the art of protein chemistry. By a "polypeptide" is meant any chain of amino acids, regardless of length or post-translational modification (e.g., glycosylation).

In a related embodiment, the invention provides a composition containing the immunogenic virus, viral protein, or viral peptide of the invention in a pharmaceutically acceptable carrier.

In another embodiment, the invention provides a method of screening for the presence of an antibody to a protein of human herpesvirus type 8, which virus is associated with body cavity based lymphoma. The method of the invention includes the following steps. A human herpesvirus type 8 particle is isolated from a body cavity based lymphoma cell (such as a BCBL-1 cell). A biological sample is obtained from a patient having or suspected of having a human herpesvirus type 8 infection, and which biological sample is suspected of containing a protein (such as an antibody) which specifically binds to human herpesvirus type 8. The biological sample of the patient is contacted with the isolated human herpesvirus type 8 virus particle. An interaction between a protein (such as an human antibody) and a virus particle is monitored by standard techniques (see, for example, Harlow and Lane, 1988, *Antibodies: A Laboratory Manual*, Cold Spring Harbor Laboratory Press, Cold Spring Harbor, N.Y.). Preferably, the human herpesvirus type 8 virus particle is isolated from a cell line designated BCBL-1. It is understood by one of ordinary skill in the art that standard control screening steps are utilized to exclude patient-derived antibodies which cross react with non-type 8 HHV particles of the invention.

In a related embodiment, the invention provides a method of screening for an antibody to an isolated protein (or peptide) from a human herpesvirus type 8 virus associated with body cavity based lymphoma. The protein may be isolated from a virus particle or it may be expressed in vitro by standard techniques from isolated DNA derived from the virus. Preferably the virus is obtained from a body cavity lymphoma cell line designated BCBL-1 (ATCC CRL 11982). It is also preferred that the isolated protein is immunogenic and does not cross react with antibodies to non-HHV-8 proteins. The screening method of the invention includes the following steps. An isolated protein (or peptide) is obtained from human herpesvirus type 8 isolated from a body cavity based lymphoma cell (such as a BCBL-1 cell). A biological sample (such as a cell or a body fluid) is obtained from a patient having or suspected of having a human herpesvirus type 8 infection, and which biological sample is suspected of containing a protein (such as an antibody) which binds to a protein from human herpesvirus type 8. The biological sample of the human is contacted with the isolated protein of human herpesvirus type 8. An interaction between a human antibody and an isolated viral protein is monitored by standard techniques (see, for example, Harlow and Lane, 1988, supra). The biological sample screened by the method of the invention includes, but is not limited to, a cell, a body fluid such as blood, serum, and ascites fluid of a human having or suspected of having a human herpesvirus type 8 infection.

By "isolated viral protein" or "isolated viral peptide" is meant that the HHV-8 viral protein or peptide provided by the invention is at least 60%, by weight, free from the proteins and naturally-occurring organic molecules with which it is naturally associated. Preferably, the preparation is at least 75%, more preferably at least 90%, and most preferably at least 99%, by weight, high-affinity melatonin receptor polypeptide. An isolated viral protein or peptide may be obtained, for example, by extraction from an HHV-8 virus particle, preferably obtained from the cell line designated BCBL-1; by expression of a recombinant nucleic acid encoding an HHV-8 viral protein or peptide, or by chemically synthesizing the protein or peptide. Purity can be measured by any appropriate method, e.g., column chromatography, polyacrylamide gel electrophoresis, or HPLC analysis.

It is an aspect of the screening methods of the invention that immunoaffinity chromatography techniques are utilized. In this aspect, the viral particle or isolated viral protein of the screening method is immobilized on a solid support as an aid to detecting virus/human antibody complex or a viral protein/human antibody complex. Such methods of immunoaffinity chromatography are well known in the art.

The invention features antibodies (monoclonal or polyclonal antibodies) that bind specifically to human herpesvirus type 8 virus particles, particularly virus particles in a cell or a body fluid from a human infected with human herpesvirus type 8.

In another aspect, the invention generally features immunoassays to determine the presence of human herpesvirus type 8, or viral protein or peptide in a biological sample, e.g., a cell or a body fluid sample, by contacting the sample with a monoclonal antibody of the invention; reacting the sample and the antibody for a time and under conditions that allow the formation of an immunocomplex between the antibody and any human herpesvirus type 8 virus particles, viral protein or peptide in the sample; and detecting the immunocomplex, the presence of the immunocomplex indicating the presence of human herpesvirus type 8 particles, viral protein or peptide in the sample.

In one embodiment of this assay, the immunocomplex can be detected by a competitive immunoassay by reacting the monoclonal antibody with the sample and with a competing antigen to which the monoclonal antibody is known to specifically bind, e.g., a detectably labelled human herpesvirus type 8 antigen or an immobilized competing antigen such as an isolated viral protein. The competing antigen can be labelled or immobilized.

In another embodiment, the immunoassay is a sandwich immunoassay that uses a second antibody, e.g., a monoclonal antibody, that either also binds human herpesvirus type 8 viral particles or binds to the first monoclonal antibody, one of the two antibodies being immobilized and the other being labeled using standard techniques. In the sandwich immunoassay procedures, the human herpesvirus type 8 viral particle-binding antibody can be a capture antibody attached to an insoluble material, and the second human herpesvirus type 8 viral particle-binding antibody can be a detector or labeling antibody.

The immunoassays can be used to determine the presence of human herpesvirus type 8 particles in biological samples including a cell or a body fluid such as blood, serum, intestinal or duodenal aspirates, peritoneal, pericardial, lymphatic or other bodily fluids.

The invention also features immunoassay kits for detecting human herpesvirus type 8 in human biological samples, comprising one or more human herpesvirus type 8 virus particle-binding monoclonal antibodies and the means for determining binding of the antibody or antibodies to human herpesvirus type 8 virus particles or viral protein in a biological sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

These and other embodiments and features of the present invention will be more fully understood when the following detailed description of the invention is read in conjunction with the accompanying drawing and claims.

BRIEF DESCRIPTION OF THE DRAWING

FIG. 1 shows the DNA sequence of a 233 bp probe, KSHV (SEQ ID NO:1) from an HHV-8 isolate (Moore, P. S. and Chang, Y. (1995) New Engl. J. Med. 332:1181–1185), which probe hybridized to the HHV-8 contained in the cell line designated BCBL-1.

DESCRIPTION OF THE EMBODIMENTS

Human herpesvirus type 8 associated lymphomas arising only in body cavities present a dilemma in diagnostic and clinical management as no systematic screening method is currently available to rapidly identify this viral agent in patients exhibiting BCB lymphoma. Body cavity based lymphoma cells obtained from eight patients exhibiting symptoms of BCB lymphoma were evaluated as part of the studies leading to the present invention. Wide variation in clinical results was observed for the eight patients such as variation in protein, glucose, LDH levels and LDH fluid/serum ratios, varied white blood count differentials due to misclassification of malignant cells as monocytes, lymphocytes or "other/unclassified" cells. Despite these clinical variations, BCB lymphoma cells from all eight patients contained human herpesvirus type 8 (HHV8) DNA sequences as determined by PCR analysis and Southern analysis (Example 1).

It is disclosed herein that HHV-8 gene sequences were present in all eight of the HIV-associated BCB lymphomas studied. HHV-8 infection has also been highly associated with endemic and HIV-associated Kaposi's sarcoma (Chang, Y. et al. (1994) Science 266:1865; Moore, P. S. and Chang, Y. et al. (1995) N. Engl. J. Med. 332:1181). However, a particular KS lesion cell type which may contain the virus was not identified. Further, an isolated, intact virus, nor a cell line capable of producing such a virus was not provided.

Kaposi's sarcoma and BCB lymphoma are not necessarily observed in the same patient. For example, of 8 patients with BCB lymphoma in the study leading to the present invention, 5 lacked clinical evidence of KS (Ng, V. L. (1994) supra). Of 8 patients with BCB lymphoma in Green et al. ((1995) supra), 6 lacked evidence of KS. Finally, of 235 HIV-infected patients examined at autopsy, no statistically significant correlation was observed between the incidence of Kaposi's sarcoma and BCB lymphoma in the same patient.

A related virus, EBV, has been proposed to play a pathogenic role in EBV-associated B-cell lymphomas in immunodeficiency (i.e., HIV infection, posttransplantation), presumably by conferring a selective growth advantage to a clone of cells infected with EBV. Such tumors exhibit monoclonality as defined by immunoglobulin gene rearrangement and monoclonal EBV infection. In HIV-associated BCB lymphomas, 6 of 6 in one study were monoclonal and monoclonally infected with EBV (Cesarman, E. (1995) supra). In contrast, only 2 of 5 lymphomas (4 monoclonal, 1 polyclonal) in another study were monoclonally infected with EBV (Green, I. et al. (1995) supra). Two of eight BCB lymphomas in the study leading to the present invention were monoclonal and monoclonally infected with EBV. Another two of the eight BCB lymphomas in this study were polyclonal and polyclonally infected with EBV. EBV was not detected in 4 of 8 cases of BCB lymphoma associated with HHV8 infection using highly sensitive PCR based methods (Example 1). Thus, HHV-8 infection is not necessarily coincident with EBV infection in BOB lymphoma cells.

As a result of the poor prognosis of BCB lymphoma and the association of HHV-8 infection, there is currently a need for methods and compositions for rapidly screening a biological sample from a cell or a body fluid of a human for the presence of HHV-8 for accurate diagnosis of HHV-8 associated diseases such as, but not limited to, BCB lymphoma and Kaposi's sarcoma and for screening to determine individuals who may be at risk to develop BCB lymphoma.

Example 1

Characterization of BCB Lymphoma Cells By Immunophenotyping

Immunophenotyping of the initial cell isolates of eight BCB lymphoma patients was performed on frozen sections of cell pellets, cytospin preparations of cell suspension, or Ficoll-Hypaque purified mononuclear cells as previously described (Herndier, B. G. et al., (1992) Blood 79:1768; Ng, V. L. et al. (1994) Blood 83:1067). Flow cytometric analysis of cell suspensions was performed on a gated subpopulation of large mononuclear cells which produced relatively little side scatter, indicative of malignant lymphoma cells using a FACS AW (Becton-Dickinson, Mountain View, Calif., U.S.A.). Fluorescein-, rhodamine-, phycoerythrin-conjugated, or biotinylated antibodies directed against different cell surface markers were obtained from Becton-Dickinson (Mountain View, Calif.).

The BCB lymphomas of eight patients whose BCB lymphoma cells contained HHV-8 DNA sequences had varying numbers of morphologically normal T-, B-cells and macrophages also present (10%–50% of all cellular elements). Only large malignant lymphoma cells were subjected to immunophenotype analysis by immunohistochemistry or by flow cytometry. The immunophenotyping by immunohistochemistry included antibodies directed against CD3, CD14, CD20, CD30(Ki-1), CD38, and CD45(LCA). Immunophenotyping performed by flow cytometry included antibodies directed against CD3, CD4, CD5, CD8, CD10, CD14, CD15, CD16+56, CD19, CD20, CD21, CD22, CD23, CD25, CD38, CD45, CD54, HLA-DR, Leu 8, kappa and lambda light chains. The profile of cell surface markers revealed that CD38 was the only cell surface marker consistently expressed by cells from all eight patients.

Characterization of Isolated BCB Lymphoma Cells for Viral DNA Sequences

Southern analysis of cellular DNA was performed by standard techniques. DNA was extracted from cells pelleted from the body cavity fluid of the patient using a standard Proteinase K digestion, phenol-chloroform extraction and ethanol precipitation procedure (Sambrook, J. et al. (1989) *Molecular Cloning: A Laboratory Manual*, second edition, Cold Spring Harbor Laboratory, Cold Spring Harbor, N.Y.). Southern blot analysis was performed with 10–20 ug of genomic DNA per analysis using digoxigenin-labelled probes and non-radiometric detection of hybridization (Genius System, Boehringer-Mannheim, Indianapolis, Ind., U.S.A.). Probes included a digoxigenin-labelled $J_H$ probe (Oncogene Sciences, San Diego, Calif. U.S.A.) and a probe containing the EBV long internal repeat, pDK14 (Dambaugh, T. et al. (1980) Proc. Natl. Acad. Sci. (U.S.A.) 77:2999) labelled with digoxigenin by nick translation according to manufacturer's recommendations (Genius system, Boehringer-Mannheim, Indianapolis, Ind.).

Cells were analyzed for the presence of HHV-8 gene sequences using polymerase chain reaction (PCR primers were described in Moore, P. S. and Chang, Y. (1995) New Engl. J. Med. 332:1181–1185) hybridize to human herpesvirus sequences in Kaposi's sarcoma cellular DNA. The predicted 233 bp PCR product from cellular DNA isolated from body cavity based lymphoma cells was produced using these primers. Thermo-cycling conditions and the internal oligonucleotide probe SEQ ID NO:1 (FIG. 1) used for Southern hybridization verification of amplified products for HHV-8 were as described by Chang et al. (Moore, P. S. and Chang, Y. (1995), supra). Cells were also analyzed by PCR to show the absence of EBV gene sequences. Primers specific for a polymorphic region of the EBNA 3C gene allowing discrimination between type 1 and type 2 EBV (125 bp PCR product, and 245 bp PCR product, respectively) and thermo-cycling conditions were performed as described by Goldschmidts et al. (Goldschmidts, W. L. et al. (1992) Leukemia 6:875). Amplification of a portion of the HLA-DQ locus having an expected product size of 242 bp was performed in parallel to verify the presence of adequate template DNA. The HLA primers and thermo-cycling conditions were as previously described (Scharf, S. J., et al. (1986) Science 233:1076). All PCR reactions contained final concentrations of 200–500 ng of genomic DNA, 200 nM dNTPs, 1X Taq polymerase buffer, 500 nM of each primer, and 1 U of Taq polymerase (Roche Molecular Systems, Branchburg, N.J., U.S.A.) in a total volume of 20 μl. 5-10 μl of the PCR reactions were analyzed on 1% agarose/2% NuSieve gels. Oligonucleotide probes homologous to sequences with the predicted PCR products were as described ($J_H$ probe: Oncogene sciences, San Diego, Calif.; pDK14 for EBV long terminal repeat: Dambaugh, T. et al. (1980) Proc. Natl. Acad. Sci. (U.S.A.) 77:2999; HLA: Scharf, S. J. et al. (1986), supra). 3' end-labelling with digoxigenin was performed according to manufacturer's recommendations (Genius System). Southern transfer and hybridization were performed by standard techniques, for example, as described in *Molecular Cloning: A Laboratory Manual* (Sambrook, J. et al. (1989), supra).

Molecular Features of BCB Lymphoma Cells

The molecular features of the malignant BCB lymphomas cells are shown in Table 1.

TABLE 1

| | | EBV | | | | |
|---|---|---|---|---|---|---|
| Patient | $J_H$ result[1] | PCR Result/ EBV type[2] | Southern result[3] | PCR/ HHV-8[4] | IL-6 (pg/ml)[5] | IL-10 (pg/ml)[5] |
| 1 | polyclonal | negative[8] | | positive | nd | nd |
| 2 | polyclonal | positive/type 1 | polyclonal | positive | 8250 | 21,810 |
| 3 | monoclonal | positive/ type 2 | monoclonal | positive | nd | nd |
| 4 | polyclonal[6] | positive/ type 1 | polyclonal | positive | 1700 | 782,100 |
| 5 | polyclonal | negative | | positive | 10,100 | 25,400 |
| 6 | monoclonal | negative | | positive | 9,350 | 124,700 |
| 7 | monoclonal | positive/ type 1 | monoclonal | positive | 7400 | 64,070 |
| 8 | monoclonal[7] | negative | | positive | 10,930 | 30,490 |

Interpretation of Southern hybridization results of BamHI/HindIII digested genomic DNA with a $J_H$ probe was as follows: monoclonal=detection of one or more rearranged bands; polyclonal=detection of a germline band with reduced intensity as compared to the placental genomic DNA control, with no detection of rearranged bands. The nonradioactive 4Southern hybridization technique used will detect a monoclonal population which makes up at least 5–10% of all cellular elements in the specimen.

PCR amplification of the appropriately sized EBNA 3C products for EBV type 1 (153 bp) or type 2 (246 bp) was verified by Southern hybridization with an internal oligonucleotide probe as previously described (Goldschmidts, W. L. et al. (1992) Leukemia 6:875).

Interpretation of Southern hybridization results with an EBV internal terminal repeat probe of BamHI digested genomic DNA were as follows: monoclonal+detection of a single band of hybridization; polyclonal=no discrete bands of hybridization detected.

The presence of HHV-8 was detected using PCR (expected 233 bp product) and verified by Southern transfer of the PCR products and hybridization with an internal oligonucleotide probe (SEQ ID NO:1), as previously described (Moore, P. S. and Chang, Y. (1995) supra).

Values in the table represent the average of triplicate testing.

Genomic DNA extracted from this tumor specimen failed to demonstrate hybridization with the JH probe in 3 independent experiments using either BamHI or BamHI/HindIII digested genomic DNA (i.e., no germlike band or any rearranged band observed).

Due to a limited amount of the original tumor tissue, the in vitro cell line established by limiting dilution cloning from patient #8's BCB lymphoma cells was a JH probe on HindIII, EcoRI, BamHI or HindIII/BamHI digested DNAs, this cell line, by definition, constitutes a monoclonal population.

The fluid specimen from patient #1 was obtained at the time of autopsy (14 days after death) and 0.7% agarose gel analysis of the extracted genomic DNA revealed degraded DNA. One of 6 independent PCR experiments demonstrated an HLA-DQ (control for template DNA) product and no EBV product; the other 5 independent PCR experiments failed to demonstrate either an EBV or an HLA-DQ product.

As seen in Table 1, HHV-8 gene sequences were present in all eight BCB lymphomas. Four of the eight BCB lymphomas were polyclonal, only four of the eight contained EVE EBNA 3C gene sequences; three having EBV type 1, one with EBV type 2 sequences, and only two of these four having EBV present as a monoclonal infection.

Possible Proliferation of BCB lymphoma cells could be due to increased expression of cytokines was examined. The cytokine, IL-6 is a growth factor involved in B-cell differentiation, and IL-10 has been proposed as an autocrine growth factor for EBV-infected immortalized B-cells (Benjamin, D. et al. (1992) Blood 80:1289). Previous reverse transcriptase PCR (RT-PCR) based surveys of HIV-associated large cell and immunoblastic B-cell lymphomas (including BCB lymphoma cells from patient #4 (identified as patient #17 in Marsh, J. W. et al. (1995) J. Interferon Cytokine Res. 15:261) demonstrated the presence of IL-6 and IL-10 transcripts and the absence of transcripts for IL-1, 2, 3, 4, and 5, implicating increased expression of IL-6 and IL-10 in their pathogenesis.

As illustrated in Table 1, the expression of cytokines was variable across the eight patients studied. IL-6 and IL-10 levels in the autologous ascites fluid were highly variable and ranged from 340–16,000-fold higher than levels present in normal human plasma.

Isolation of Body Cavity Lymphoma Cells

Malignant BCB lymphoma cell line BCBL-1 was established in vitro from the malignant effusion of a patient diagnosed with cutaneous cell (but not visceral) Kaposi's sarcoma. Lymphoma was diagnosed in the patient from fluid obtained from the abdomen when the patient exhibited progressive abdominal discomfort approximately 4.5 years after diagnosis of KS. Diagnostic paracentesis provided fluid containing cells consistent with high grade lymphoma.

Isolation of BCB Lymphoma Cells

Mononuclear cell preparations were prepared from the abdominal fluid of the patient by an initial pelleting of cells (1000xg, 10 minutes, room temperature), resuspension of the cell pellet in PBS, pH 7.5, and standard ficoll-hypaque gradient centrifugation. Cells pelleting at the interface were washed twice with PBS and DNA extracted immediately, or resuspended in 20% DMSO/RPMI(Roswell Park Memorial Institute) medium/10% fetal calf serum and stored in liquid nitrogen. Cell supernatants obtained after the initial centrifugation were saved and stored at −70° C.

Example 2

Establishment of Cell Line BCBL-1

Cells isolated from the abdominal fluid of patient #8 and analyzed for the presence of HHV-8 and absence of EBV were initially cultured in RPMI 1640/20% autologous ascites/50 µg/ml gentamicin/0.05 mM 2-mercaptoethanol supplemented with 1 mM sodium pyruvate and 2 mM L-glutamine at 37° C. in 5% $CO_2$. Changes of cell culture medium was performed weekly or biweekly depending on the growth of the cells in vitro. The culture was gradually made to grow in vitro in a medium which substituted 10% fetal calf serum for the 20% autologous ascites. The cell line was further cloned by limiting dilution.

Following establishment of the BCBL-1 cell line, cells continued to display the viral genome characteristic of its primary tumor.

Preferably, the HHV-8 is latent in normally growing BCBL-1 cells in vitro. Latency of a virus is defined as persistant infection of a cell population, but virus is released only rarely. In such cells virus multiplication (lytic growth) can start under inductive conditions, but is arrested at some stage in the absence of induction. Latency of the human herpesvirus type 8 in B-cell lymphoma cells was demonstrated by transmission electron microscopy, increased viral DNA replication (Southern analysis) and late gene expression upon induction of the cell line with TPA (Northern analysis). Under conditions in which the virus is latent, approximately 1% (and not more than 4%) of the cells in a population contain visible viral particles by electron microscopy. Of the cells containing visible viral particles by electron microscopy, only approximately 1–2 particles were visible, and not more than 50 particles were visible per cell. Under latent (uninduced) conditions 1–4% of the cell culture cells contain approximately 1–2 viral particles and less than 50 viral particles.

Example 3

Lytic Growth of HHV-8 in BCBL-1 Cells

Lytic replication of HHV-8 in BCBL-1 and virion production is inducible by such compounds as phorbol esters (with or without calcium ionophores), butyrate, 5-azacytidine, and the like. Preferably TPA (phorbol 12-myristate 13-acetate) is used to induce viral production. When phorbol ester TPA was added to a BCBL-1 culture (20 ng/ml), a dramatic inhibition of cellular growth was observed over the next 48 hours, with the appearance of considerable cytotoxicity. PolyA+ RNA was prepared from such cells and reverse-transcribed into radiolabeled cDNA by standard techniques using random primers and AMV reverse transcriptase for use as a probe of HHV-8 cloned DNA segments. This radiolabelled cDNA represents cellular and viral DNA expression during induction of lytic growth of the virus. When this cDNA probe was applied to an array of filter-bound SalI fragments of approximately 90% of the HHV-8 genome cloned in lambda vectors, it was observed by Southern analysis that every cloned HHV-8 fragment tested hybridized to the probe, indicating widespread transcription of the viral genome during lytic growth.

To examine TPA induction of lytic growth, viral DNA replication and late gene expression, parallel cultures of BCBL-1 cells were treated with medium containing or lacking TPA. After 48 hours, total intracellular DNA or polyA+ RNA was prepared by standard techniques. DNA preparations were digested with BamHI and equal amounts of genomic DNA was examined by Southern blotting with a radiolabelled HHV-8 segment containing the capsid gene. An approximately 15-fold increase in viral DNA is evident following TPA treatment. A Northern analysis of polyA+ RNA prepared from cells with and without TPA induction was performed, with RNA samples hybridized to a radiolabelled probe corresponding to the late expressing viral major capsid gene of HHV-8. A 50-to 70-fold induction of transcription was observed, an amount which is more than can be accounted for by DNA template copy number amplification. The presence of a faint signal for major capsid protein mRNA in uninduced BCBL-1 cells indicates that lytic growth has been activated spontaneously in a small fraction of the cells.

Example 4

Electron Microscopy of HHV-8 in BCBL-1 Cells

Transmission electron microscopy (JEOL JEM-100 SX) using glutaraldehyde-fixed induced and non-induced, BCBL-1 cell line (EBV-negative) consistently demonstrated viral particles having the features of a human herpesviruses type 8 as a herpesviral particle of approximately 100 nm diameter, having a viral genome visible by electron microscopy as an electron-dense central icosahedral toroid, and the DNA of the virus hybridizing to DNA of SEQ ID NO:1. Magnification (20,000 X) of a cell nucleus 48 hours post-TPA treatment revealed clumping and centripetal redistribution of host chromatin as well as the accumulation of an abundance of virus particles. A high concentration of nuclear based particles were intermingled with condensed chromatin. Virions were also detected in the cytoplasm, usually enclosed within trilaminar membrane vesicles.

Higher magnification views of the nuclei revealed the virus particles to have a diameter of 100 nm, typical of herpesvirus. Complete virions featured a hexagonal nucleoid. The hexagonal structure is compatible with the icosahedron arrangement of 162 capsomers present in other herpesviruses described to date (Palmer, E. L. and Martin, M. L. (1988) *Electron Microscopy in Viral Diagnosis*, CRC Press, Boca RAton, Fla.).

The uninduced BCBL-1 cell line features approximately 1% of the cells producing virus, each infected cell section showing approximately 1–2 particles as visualized by transmission electron microscopy. Upon induction by TPA, more than 4% and fewer than 50% of the cells have ultrastructurally visible viral particles by transmission electron microscopy, with each infected, induced cell containing at least 100 viral particles. More preferably, at least 5%–10% of the cells have visible virus particles, with each infected cell containing more than 100 viral particles. Preferably, the cell line of the invention produces 300 or more particles per induced cell, more preferably the cell line produces 500 or more viral particles per induced cell. Preferably, an induced cell of the cell line of the invention produces fewer than 100,000 viral particles per cell. Because the BCBL-1 cell line is not infected with EBV, the transmission electron microscopy results provided herein represent the first demonstration of HHV-8 induction in a cell. The virus is shown herein to be inducible in a B lymphoma cell line derived from a BCB lymphoma. In addition, the cell line of the invention is the first cell line containing HHV-8, is the first cell line capable of producing intact HHV-8 virus particles, and which cell line is capable of being grown in vitro.

Example 5

Isolation of HHV-8 Virus Particles from BCBL-1 Cells

Activation of a complete lytic program results in the release of viral particles into the medium. Culture supernatants of uninduced or TPA-induced BCBL-1 cells were collected. Viral particles in the supernatant were concentrated by ultracentrifugation. Electron microscopy of induced cultures revealed abundant virus particles (Example 4). The concentration of virus particles in the cell culture supernatant was approximately $10^6$ virus particles/ml of supernatant. Preferably the cell line of the invention produces at least approximately 100 and less than $10^{10}$ virus particles/ml, preferably $10^6$ virus particles/ml. The particulate nature of the virus in the supernatant was confirmed by showing that the released viral genomes were resistant to exogenous nucleases. Concentrated pellets from uninduced or induced cells were exposed to exogenous DNase I. Under these conditions, unencapsidated chromosomal DNA fragments in the preparation were completely degraded, as was naked cloned HHV-8 DNA (not shown). In contrast, encapsidated viral DNA in these preparations was almost entirely resistant to nuclease attack. The amount of encapsidated DNA increased at least 20-fold following induction as observed by Southern analysis. It is estimated that HHV-8 accumulates in a BCBL-1 cell to at least 10 virus particles per induced cell within 48 hours post-TPA induction. Preferably the BCBL-1 cell least 100 particles. In general, lytic growth will produce no more than 100,000 virus particles per cell post-induction. Virus particles were isolated from the medium by standard sucrose sedimentation techniques.

Example 6

Isolation of Viral Proteins and Peptides from HHV-8 Virus Particles

Human herpesvirus type 8 is obtained from the cell culture supernatant of a cell line containing a human herpesvirus type 8, which cell line has been induced to cause lytic growth of the virus and release of the virus into the cell culture medium. Preferably the cell line is BCBL-1, designated ATCC CRL 11982. Virus is partially purified from induced cell culture supernatant by differential centrifugation and banding in CsCl gradients, or other standard techniques well known to those of ordinary skill in the art. Fractions are collected and examined by electron microscopy, or the viral DNA is analyzed by Southern hybridization using an HHV-8 probe (SEQ ID NO:1) . Fractions containing virus particles which have the characteristics of HHV-8 as described herein are pooled, dialyzed for example, against 0.01 M phosphate-buffered saline, pH 7.2, and used as virus inoculum for hybridoma production.

In general, viral proteins are isolated from the HHV-8 virus particles as follows. The isolated HHV-8 virus is denatured, DNA and proteins are fractionated, and the proteins are purified by standard protein purification techniques. Viral proteins from purification fractions may be tested for immunogenicity by standard techniques and each fraction further fractionated and tested until an isolated immunogenic viral protein is obtained.

Example 7

Determination of Virus and Viral Protein Immunogenicity

The virus is isolated from the BCBL-1 cell line following induction of lytic viral growth (Example 5). For some manipulations the virus may be attenuated. By attenuated virus is meant an immunogenic virus which does not elicit disease symptoms because it is infective but does not elicit disease symptoms; because it is non-infective; or because it has been treated to be non-pathogenic but is still immunogenic.

Alternatively, immunogenicity of an HHV-8 viral protein or peptide may be determined by screening a biological sample such as a cell or a body fluid of a human patient infected with HHV-8 for antibody interaction with a candidate viral protein (Example 9). Those viral proteins which have elicited an immune response (produced an antibody against an HHV-8 viral protein) in a human patient are selected as immunogenic proteins. These viral proteins are useful in a screening method for viral infection in which the isolated protein or an immunogenic peptide of the protein is contacted with a biological sample (such as a cell or a body fluid) from a patient to determine the presence of an antibody to the immunogenic protein in the biological sample.

Example 8

Production of Antibodies to HHV-8 Virus Particles and Isolated Proteins

Antibodies are raised to a virus or viral protein by known techniques which allow one to obtain monoclonal or polyclonal antibodies specific to an HHV-8 virus, viral protein, or viral peptide (see, for example, Harlow and Lane, 1988, *Antibodies: A Laboratory Manual*, Cold Spring Harbor Laboratory Press, Cold Spring Harbor, N.Y.).

Antibodies are proteins produced in animals by antibody-producing cells known as B-lymphocytes in response to the exposure of the animal to foreign compounds (antigens). These antibodies bind specifically to the particular viral particle, protein, or peptide which stimulate their production.

Antibody-producing cells arise in the spleen of an animal when the animal has been immunized with an immunogenic compound. The antibodies produced by such a response are known as polyclonal antibodies. Polyclonal antibodies raised against a particular protein do not all bind with the same specificity to that protein. However, it is possible to obtain antibodies which all bind with the same specificity and affinity to a protein. These antibodies are known as monoclonal antibodies.

In order to obtain such monoclonal antibodies, antibody-producing cells are firstly extracted from the spleen of an immunized animal. These cells are then fused with myeloma cells to produce hybridomas. Fusion may be achieved, for example, by treatment with polyethylene glycol. The hybridomas are capable of producing antibodies, like the precursor antibody-producing cells, but are immortal; they are capable of continuous growth in vitro. A number of myeloma cells suitable for fusing with antibody producing cells are known and readily available to those skilled in the art. An example of a suitable myeloma cell which is readily available is PX3-63-AG8-653. This cell is available, for example, from the American Type Culture Collection, Rockville, Md., U.S.A. under the number ATCC CRL 1580.

Once the antibody-producing cells and the myeloma cells have been fused, the resultant hybridoma cells are separated from the infused cells and cloned by repeated limiting dilution. Cloned hybridomas are then tested to determine which are producing the desired antibodies. This testing may be achieved, for example, by competitive enzyme linked immunosorbent assay (ELISA). Specificity and affinity for an HHV-8 protein may be assessed by the addition of free virus or viral protein to the ELISA test system to evaluate the ability of the free protein to inhibit binding of the monoclonal antibody to protein which is bound to a solid phase.

Once a particular hybridoma has been selected, monoclonal antibodies may readily be produced in large quantities using well known techniques. If desired, these antibodies may be labelled with an enzyme; e.g. horse radish peroxidase or alkaline phosphatase; alternatively, the antibodies may be labelled with any detectable marker, such as a radiolabel, or a light absorbing molecule.

Techniques for producing polyclonal and monoclonal antibodies for a protein are well known to those skilled in the art. Examples of references in which such techniques are described include Methods of Enzymology Volume 70 and Volume 73 Immunochemical Techniques parts A and B respectively Edited by Van Vunakis, H. and Langone, J. L., Published by Academic Press 1980 (Part A) and 1981 (Part B), and Kohler, G. and Milstein, C, Nature, Vol. 265, p. 495 (1975).

In one exemplary but non-limiting, procedure, hybridoma production is performed as follows. BALB/c mice (eight-week-old females) are inoculated subcutaneously with 0.1 ml of isolated human herpesvirus type 8 (preferably HHV-8) virus emulsified in an equal volume of TiterMax adjuvant (Vaxcel, Inc., Norcross, Ga.). Mice are given a second subcutaneous inoculation three weeks later. The mice are given two more inoculations (intraperitoneal) of HHV-8 virus in Freund's incomplete adjuvant, and one intraperitoneal inoculation of virus without adjuvant, all two weeks apart. Five days after the last inoculation, mouse spleens are fused to SP 2/0 myeloma cells with Kodak polyethylene glycol 1450 plus DMSO, according to the procedures described by Lane, *J. Immunol. Methods*, 181:223–228, 1985. Hybrid cells are seeded onto 24 well plates in HAT medium containing 10% Hybridoma Cloning Factor (IGEN, Inc., Rockville, Md.). After seven days, hybridomas are screened for antibodies which reacted with human herpesvirus type 8 antigen from the cell culture supernatant of a body cavity based lymphoma cell line containing human herpesvirus type 8 (preferably BCBL-1, designated ATCC CRL 11982).

Hybridomas that secrete such antibodies are cloned twice by use of the limiting dilution technique. Ascitic fluids for clones are prepared in BALB/c mice. Standard hybridoma technology is readily available to one of ordinary skill in the art (see, e.g., Kohler et al., *Nature* (1975) 256:495, 1975; Kohler et al., *Eur. J. Immunol.* (1976) 6:292; Kohler et al., *Eur. J. Immunol.* (1976) 6:511; Hammerling et al., *in Monoclonal Antibodies and T Cell Hybridomas*, Elsevier, N.Y., (1981); and Ausubel et al., supra). Antibodies are purified by peptide antigen affinity chromatography.

An antibody which binds specifically to HHV-8 virus particle, free viral protein, or viral peptide is useful in a screening method for the presence of HHV-8 or HHV-8 protein in a biological sample from a patient infected with HHV-8 or suspected of being infected with HHV-8.

Another exemplary but non-limiting procedure for an indirect enzyme based immunoassay (EIA) useful for screening hybridomas, wells of polyvinyl chloride microtiter plates are coated with a suspension of human herpesvirus type 8. The wells are coated for 24 hours at room temperature (20–22° C.) or other conditions necessary to coat the wells with virus particles or proteins, and post-coated with 1% w/v bovine serum albumin in 0.01 M phosphate-buffered saline (PBS) for 24 hours at 4° C. The plates are washed with PBS and 0.05 ml of hybridoma supernatant fluids diluted in 50% fetal calf serum and 50% 0.025 M Tris-HCl buffer (pH 7.2) with 0.015% Tween 20, are added and incubated for 1 hour at 37° C. Peroxidase-labelled goat antibody specific for mouse IgG (Kirkegaard and Perry Laboratories, Gaithersburg, Md.), at 1 $\mu$g/mL in the Tris buffer used above, is added and incubated for 1 hour at 37° C. The plates are washed five times with PBS, soaked for 30 seconds with PBS containing 0.05% Tween 20, and washed again. Substrate for peroxidase (0.05 mL, O-phenylene-diamine-$H_2O_2$; Abbott Laboratories, North Chicago, Ill.) is added for 10 minutes, and the reaction is stopped with 0.1 mL of 1 N $H_2SO_4$. Biotin/avidin labeling systems can also be used.

The absorbance of the solution is measured at 492 nm in a plate-reader spectrophotometer. After monoclonal antibodies are obtained, a direct EIA is used for testing biological samples; however, other standard immunoassays can also be used. The same monoclonal antibodies are used for coating plates and for antigen detection. The antibodies are purified from ascitic fluid by ammonium sulfate precipitation, and either used directly for coating plates or labelled with peroxidase for use as detector antibodies. The antibodies are labelled with peroxidase by the periodate method of Wilson and Nakane, "Recent developments in the periodate method of conjugating horseradish peroxidase (HRPO) to antibodies," p. 215–224. In: Knapp et al. (eds.), *Immunofluorescence and Related Staining Techniques* (Elsevier/North Holland Biomedical Press, Amsterdam, 1978).

For the EIA, wells are coated with monoclonal antibodies (2 $\mu$g/mL) for 18 to 24 hour at 20–22° C., washed, and post coated with Superblock (Pierce Chemical Co., Rockford, Ill.) 4 to 6 hours. The plates are washed, and biological samples or controls (known positive and negative biological samples) are added and incubated for 18 hours at 20–22° C. Plates are washed, and the peroxidase conjugated antibodies added and incubated at 37° C. for 2 hours. The remaining procedures are as described for the indirect EIA. Samples are considered positive for monoclonal antibody to human herpesvirus type 8 in the screening tests, or for human herpesvirus type 8 antigen in the virus-specificity tests, if the absorbance value is both $\geq 0.1$ and three or more times the negative control (wells coated with pre-immune serum in the screening tests, and wells coated with an unrelated monoclonal antibody in the virus specificity tests).

Example 9

Screening a Biological Sample for the Presence of HHV-8 Virus Particle, Viral Protein, or Antibody to HHV-8

As discussed above, one aspect of the invention features screening a biological sample such as a cell or a body fluid of a human for the presence of HHV-8, an HHV-8 protein or peptide, or an antibody to the virus. If it is desired to screen for the presence of the virus or a viral protein, the screening agent is an antibody raised to the virus or to an immunogenic viral protein or peptide. If it is desired to screen the biological sample for the presence of an antibody to the virus or viral protein, the screening agent is an isolated HHV-8 viral particle, isolated viral protein, or isolated viral peptide. Preferably, the viral protein or peptide is immunogenic.

For convenience, it is preferred that the screening agent is immobilized on a solid support. Solid supports useful in the invention include, but are not limited to, the surface of an assay vessel (i.e. the wells of a 24 well plate); and a plurality of beads onto which the virus or viral protein is covalently attached by standard techniques.

The elements of the screen include a screening agent preferably immobilized onto a solid support. If detection of virus or viral protein in the biological sample is desired, the screening agent is an antibody to the virus or viral protein and the binding agent is the virus or viral protein. If detection of a virus-specific antibody in a biological sample is desired, the screening agent is HHV-8, viral protein, or viral peptide and the binding agent is the antibody suspected of being present in the biological sample.

The elements of the screen further include methods and means of detecting complex formation between the binding agent and the screening agent. Complex formation is monitored by a variety of methods understood by one of ordinary skill in the art and within the scope of the present invention. Binding may be monitored by the ability of the binding agent (present in the biological sample such as a cell or a body fluid) to mask a signal presented by the screening agent. Thus, binding is detected as a reduction in signal relative to a control. Alternatively, binding may be monitored by removing the binding agent from contact with the immobilized screening agent, followed by contacting the binding agent with a different preparation of the screening agent in which the screening agent is non-immobilized and detectably labelled. The amount of labelled screening agent bound to a binding agent is then measured relative to unbound labelled screening agent. Where the binding agent is a human antibody in a biological sample, the presence of the human antibody bound to the immobilized virus screening agent is detected by contacting the immobilized human antibody/immobilized virus with a detectably labelled mouse-anti-human (or like anti-human antibody) antibody and measuring the amount of signal in the test sample relative to a control sample lacking a human antibody. Other methods of monitoring binding of a binding agent to a screening agent of the invention are well known to one of ordinary skill in the art.

An exemplary method for screening for the presence of an antibody to HHV-8 in a biological sample (such as a cell or a body fluid) of a patient suspected of being infected with HHV-8 includes the following steps. An isolated, intact HHV-8 is obtained from the culture supernatant of a body cavity based lymphoma cell line containing HHV-8 following induction of lytic growth of the virus. The isolated viral particles may be used as the screening agent, or an immunogenic viral protein or peptide may be isolated from the virus particle for use as the screening agent. The screening agent (virus or viral protein) is immobilized onto a solid support. A biological sample is obtained from a patient suspected of being infected with a human herpesvirus type 8. As a control, a biological sample from a human uninfected with a human herpesvirus type 8 is also obtained and examined as for the test sample. An aliquot of the biological sample suspected of containing an antibody (the binding agent) to HHV-8 is contacted with the isolated HHV-8 or isolated viral protein (the screening agent) under conditions which allows the antibody to bind to the virus or viral protein. If the screening agent is immobilized onto a solid support, the unbound materials of the body fluid are removed by washing, leaving the immobilized virus/human antibody complex on the solid support. The presence of the complex is monitored by contacting the complex with a detectable anti-human antibody (for example, a mouse-anti-human antibody which is directly labelled or detectable by subsequent reaction with a label). The presence of an antibody to HHV-8 is detected relative to a control sample.

It is understood that the isolated, intact HHV-8 virus and ultimately the viral proteins, viral peptides, and viral DNA useful in the obtaining viral proteins are obtained from a cell line of the invention. The cell line is a B-lymphoma cell line clonally generated from a body cavity based B-lymphoma cell containing the latent HHV-8 virus. The cell line grows in vitro and is capable of producing more than 50 and less than 2000 virus particles induced cell upon induction of lytic growth of the virus. The cell line is further characterized by containing a human herpesvirus having the characteristics of a herpesviral particle of approximately 100 nm diameter, having a viral genome visible by transmission electron microscopy as an electron-dense central icosahedral toroid, and the DNA of the virus hybridizing to DNA of SEQ ID NO:1. Preferably the cell line is BCBL-1 and is designated ATCC CRL 11982.

Lymphoma cell line BCBL-1 has been deposited as ATCC Deposit No. CRL 11982 at The American Type Culture Collection, 12031 Parklawn Drive, Rockville, Md. 20852.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An isolated human B cell line, wherein the cell line contains a human herpesvirus type 8 virus particle and does not contain Epstein Barr Virus, wherein the cell line is the human B-lymphoma cell line designated BCBL-1 (ATCC CRL 11982).

2. The cell line of claim 1 further characterized by:
    a) an ability to grow in a culture medium in vitro;
    b) maintaining the virus in a latent state in the absence of a lytic growth inducing agent;
    c) containing human herpesvirus type 8 virus particles which are visible by transmission electron microscopy; and
    d) isolated from a body cavity being selected from the group consisting of peritoneal cavity, pleural cavity, and pericardial cavity.

3. The cell line of claim 1 further characterized by:
    each cell contains 10 or more intact human herpesvirus type 8 virus particles after treatment with a lytic growth inducing agent.

4. The cell line of claim 1, wherein each cell contains 100 or more copies of human herpesvirus type 8 after treatment with a lytic growth inducing agent.

5. The cell line of claim 1, wherein upon treatment with a lytic growth inducing agent, contains 1000 or more copies of human herpesvirus type 8 virus particles.

6. The cell line of claim 4 wherein the lytic growth inducing agent is selected from the group consisting of a phorbol ester, butyrate, an agent causing surface Ig crosslinking, 5-azacytidine, and TPA.

7. The cell line of claim 2 wherein the cell culture medium comprises RPMI 1640/10% fetal calf serum/50 µg/ml gentamicin/0.05 mM 2-mercaptoethanol supplemented with 1 mM sodium pyruvate and 2 mM L-glutamine at 37 C in 5% $C_2O$.

8. An isolated human herpesvirus type 8 virus particle, characterized by:

---

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 233 base pairs
       (B) TYPE: nucleic acid
       (C) STRANDEDNESS: single
       (D) TOPOLOGY: linear (ii) MOLECULE TYPE: cDNA (vi) ORIGINAL SOURCE:
       (A) ORGANISM: KSHV (xi) SEQUENCE DESCRIPTION: SEQ ID NO:1:

AGCCGAAAGG ATTCCACCAT TGTGCTCGAA TCCAACGGAT TTGACCCCGT GTTCCCCATG        60

GTCGTGCCGC AGCAACTGGG GCACGCTATT CTGCAGCAGC TGTTGGTGTA CCACATCTAC       120

TCCAAAATAT CGGCCGGGGC CCCGGATGAT GTAAATATGG CGGAACTTGA TCTATATACC       180

ACCAATGTGT CATTTATGGG GCGCACATAT CGTCTGGACG TAGACAACAC GGA             233 a) having a diameter of approximately 100 nm;
b) having a viral genome visible by electron microscopy as an electron-dense icosahedral central toroid core;
c) having a DNA which hybridizes to a DNA segment of SEQ ID NO: 1; and
d) isolated from a human B-lymphoma cell obtained from a body cavity based lymphoma of a patient presenting with Kaposi's sarcoma skin lesions, wherein the human B-lymphoma cell is BCBL-1 (ATCC CRL 11982).

* * * * *